United States Patent [19]

Peck et al.

[11] Patent Number: 5,034,386

[45] Date of Patent: * Jul. 23, 1991

[54] METHODS FOR ADMINISTRATION USING 1-SUBSTITUTED AZACYCLOALKANES

[75] Inventors: James V. Peck, Costa Mesa; Gevork Minaskanian, Irvine, both of Calif.

[73] Assignee: Whitby Research, Inc., Richmond, Va.

[ * ] Notice: The portion of the term of this patent subsequent to Dec. 12, 2006 has been disclaimed.

[21] Appl. No.: 233,553

[22] Filed: Aug. 17, 1988

Related U.S. Application Data

[63] Continuation of Ser. No. 824,845, Jan. 31, 1986, abandoned.

[51] Int. Cl.$^5$ .............................................. A61K 31/55
[52] U.S. Cl. ..................................... 514/212; 514/946; 514/947
[58] Field of Search .................... 514/212, 946, 947

[56] References Cited

U.S. PATENT DOCUMENTS

| | | | |
|---|---|---|---|
| 3,051,616 | 8/1962 | Drapal | 167/37 |
| 3,085,931 | 4/1963 | Darlington | 167/37 |
| 3,157,641 | 2/1964 | Wallis et al. | 260/239.3 |
| 3,306,910 | 2/1967 | Louthan | 260/326.83 |
| 3,306,911 | 2/1967 | Doss | 260/326.83 |
| 3,332,938 | 7/1967 | Mayhew et al. | 260/239.3 |
| 3,342,673 | 9/1967 | Kaufman et al. | 167/42 |
| 3,551,544 | 12/1970 | Herschler | 424/7 |
| 3,598,122 | 8/1971 | Zaffaroni | 128/155 |
| 3,598,123 | 8/1971 | Zaffaroni | 128/155 |
| 3,678,156 | 7/1972 | MacMillan et al. | 424/68 |
| 3,731,683 | 5/1973 | Zaffaroni | 128/155 |
| 3,742,951 | 6/1973 | Zaffaroni | 128/155 |
| 3,814,097 | 6/1974 | Ganderton et al. | 128/268 |
| 3,823,152 | 7/1974 | Morimoto | 260/293.69 |
| 3,865,814 | 2/1975 | Lussi et al. | 260/239.3 R |
| 3,891,757 | 6/1975 | Higuchi | 424/343 |
| 3,921,636 | 11/1975 | Zaffaroni | 128/2 R |
| 3,954,966 | 5/1976 | Lim et al. | 424/78 |
| 3,960,922 | 6/1976 | Baker et al. | 260/465 D |
| 3,966,806 | 6/1976 | Baker et al. | 260/558 R |
| 3,972,995 | 8/1976 | Tsuk et al. | 424/28 |
| 3,989,815 | 11/1976 | Rajadhyaksha | 424/60 |
| 3,989,816 | 11/1976 | Rajadhyaksha | 424/60 |
| 3,991,203 | 11/1976 | Rajadhyaksha | 424/59 |
| 3,993,072 | 11/1976 | Zaffaroni | 128/260 |
| 3,993,073 | 11/1976 | Zaffaroni | 128/260 |
| 3,996,934 | 12/1976 | Zaffaroni | 128/268 |
| 4,021,224 | 5/1977 | Pallos et al. | 71/88 |
| 4,031,894 | 6/1977 | Urfahart . | |
| 4,060,084 | 11/1977 | Chandrasekoran et al. | 128/260 |
| 4,069,307 | 1/1978 | Higuchi . | |
| 4,077,407 | 3/1978 | Theeumes . | |
| 4,118,500 | 10/1978 | Pritzlaff et al. . | |

(List continued on next page.)

FOREIGN PATENT DOCUMENTS

| | | |
|---|---|---|
| 947764 | 5/1974 | Canada . |
| 29617 | 6/1981 | European Pat. Off. . |
| 29618 | 6/1981 | European Pat. Off. . |
| 010437 | 3/1984 | European Pat. Off. . |
| 129284 | 12/1984 | European Pat. Off. . |
| 164998 | 12/1985 | European Pat. Off. . |
| 2003128 | 7/1971 | Fed. Rep. of Germany . |
| 1243632 | 9/1960 | France ............................... 540/525 |
| 45-22121 | 7/1970 | Japan . |
| 56-020572 | 2/1981 | Japan . |
| 61-033128 | 2/1986 | Japan . |
| 61-129140 | 6/1986 | Japan . |
| 549688 | 3/1986 | Spain . |
| 528848 | 11/1977 | U.S.S.R. ............................... 548/519 |
| 1102521 | 2/1968 | United Kingdom ................ 540/525 |
| 1421743 | 1/1976 | United Kingdom . |
| 1427744 | 1/1976 | United Kingdom . |
| 2078725 | 1/1982 | United Kingdom ................ 548/530 |

OTHER PUBLICATIONS

*Current Therapy*, p. 662 (1981).
*Current Therapy*, pp. 599–603 (1984).
Barry et al., *Proc. Royal Irish Academy*, vol. 55, pp. 137–148 (1953)—see p. 146*.

(List continued on next page.)

*Primary Examiner*—Stanley J. Friedman
*Attorney, Agent, or Firm*—Walter A. Hackler; Robert J. Baran

[57] ABSTRACT

This invention provides compositions comprising a physiologically-active agent and a compound having the structural formula

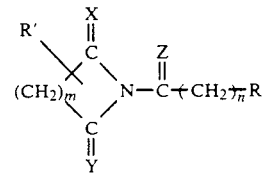

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2–6; R' is H or a lower alkyl group having 1–4 carbon atoms; n is 0–17 and R is —CH$_3$,

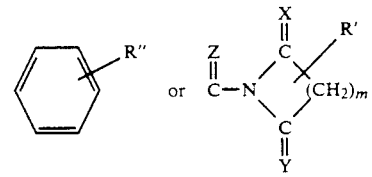

wherein R" is H or halogen in an amount effective to enhance the penetration of the physiologically-active agent through the skin or other membrane of the body of an animal.

4 Claims, No Drawings

U.S. PATENT DOCUMENTS

| | | | |
|---|---|---|---|
| 4,122,170 | 10/1978 | Rajadhyaksha | 424/180 |
| 4,201,211 | 5/1980 | Chandrasekoran et al. | |
| 4,264,594 | 4/1981 | McGonim et al. | |
| 4,284,648 | 8/1981 | Hussain et al. | |
| 4,292,299 | 9/1981 | Sajuki | |
| 4,311,481 | 1/1982 | Matelne | 424/180 |
| 4,316,893 | 2/1982 | Rajadhyaksha | 424/180 |
| 4,405,616 | 9/1983 | Rajadhyaksha | 424/244 |
| 4,415,563 | 11/1983 | Rajadhyaksha | 424/180 |
| 4,423,040 | 3/1983 | Rajadhyaksha | 424/185 |
| 4,424,210 | 1/1984 | Rajadhyaksha | 424/155 |
| 4,525,199 | 6/1985 | Rajadhyaksha | 514/788 |
| 4,537,776 | 8/1985 | Cooper | 514/557 |
| 4,552,872 | 11/1985 | Cooper | 514/557 |
| 4,557,934 | 12/1985 | Cooper | 424/155 |

OTHER PUBLICATIONS

Kometani, et al., "A Synthesis of Succinimides and Glutarimides From Cyclic Anhydrides," Chem. Abs., 106:84339k (1986).

Tremol Lozano, "Process for the Preparation of Benzoylpyrrolidinones," Chem. Abs., 106:6713m (1986).

Betrakova, et al., "Synthesis of Alkylene Diglutarimides," 69:86313p, (1968).

Chemical Abstracts 82:93905e.

Chemical Abstracts 83:1758d.

Chemical Abstracts 83:91780g.

Chemical Abstracts 102:183860x.

Chemical Abstracts 104:213242h.

Bennett, S. L., et al, "Optimization of Bioavailability or Topical Steroids: Non-Occluded Penetration Enhancers Under Thermodynamic Control," J. Pharm Pharmcol. 37(5), 298–304, 1985.

Goldman, L., et al., "Preliminary Investigative Studies with DDT in Dermatologic and Plastic Surgery", Lasers Surg Med 5(5): 453–456, 1985.

Chow, DS-L, et al., "Consentration-Dependent Enhancement of 1-Dodecylazacyloheptan-2-One on the Percutaneous Penetration Kinetics of Triamcinolone Acetonide", J. Pharm Sci 73(12):1794–1799, 1984.

DeClercq, E., "Topical Treatment of Cutaneous Herpes Simplex Virus Infection in Hairless Mice with (E)-- 5-(2-Bromovinyl)-2'-Dioxyurdine and Related Compounds", Antimicrob Agents Chemother 26(2): 155–159, 1984.

Goodman, M., et al., Differential Scanning Colorimetry (DSC) of Human Stratum Corneum: Effect of Azone. Presentation at the British Pharmaceutical Conference Leeds, 1985.

Hadgraft, J., et al., "Facilitated Transport of Sodium Salicylate Across an Artificial Lipid Membrane by Azone", J. Pharm Pharmacol 37(10): 725–727, 1985.

Higuchi, W. I., "Macro- and Micro-Physical Chemical Considerations in Understanding Drug Transport in the Stratum Corneum", Second Int'l Symp. Recent Advances in Drug Delivery Systems, Salt Lake City, Utah, 1985.

Higuchi, W. I., et al., "Topical Delivery of Antiviral Agents: In Vivo/In Vitro Correlations", Proc. Int. Symp., pp. 1–7, 1984.

Hoelgaard A., "Dermal Drug Delivery—Improvement by Choice of Vehicle or Drug Derivative", 2nd Int'l Symp Recent Adv Drug Delivery Systems, 1985.

Liang, W. Q., et al., "Affect of Azone on Local Pharmacokinetics of Para-Aminobenzoic Acid in Skin", 11th Int'l Symp. Controlled Release Bioactive Mat., 1984.

Maibach, H. I., et al., "Phototoxicity (Photoirritation) of Topical and Systemic Agents", Advances in Modern Toxicology, 4:211–223, 1977.

Marzulli, F. N., et al., Contact Allergy: Predictive Testing in Humans, Advances in Modern Toxicology 4:253–372, 1977.

McCullough, J. L. et al., "Regulation of Epidermal Prolifieration in Mouse Epidermis by Combination of Difluoromethyl Ornithine (DFMO) and Methylglyoxal Bis (Guancylhydrazone) (MGBG)", J. Invest. Dermatol. 85(6): 518–521, 1985.

McCullough, J. L., et al., "Development of a Topical Hematoporphysin Derivative Formulation: Characterization of Photosensitizing Effects". In Vivo., J. Invest Dermatol 81(6): 528–532, 1983.

Ohshima, T. et al., "Enhancing Effect of Absorption Promoters on Percutaneous Absorption of a Model Dye (6-Carboxyfluorescein) as Poorly Absorbable Drugs. III. Study on the Absorption Promoting Effect of Azone", J. Pharm. Dyn 8:900–905, 1985.

Ryatt, J. K., "Pharmacodynamic Measurement of Percutaneous Penetration Enhancement In Vivo", J. Pharm Sci 75:(4), 374–377, 1986.

Stoughton, R. B., "Azone as a Promoter of Percutaneous Absorption", (1983), Acta Pharm 20(1):62.

Shannon, W. M., et al., "Influence of 1-Dodecylazacydoheptan-2-one (Azone) on the Topical Therapy of Cutaneous Herpes Simplex Virus Type 1 Infection in Hairless Mice with 2',3'-D-Arabinofuranosyladenine", J Pharm Sci 74(11):1157–1161, 1985.

Spruance, S. I., et al., "Effect of Azone and Propylene Glycol on Penetration of Trifluorothymidine Through Skin and Efficacy of Different Topical Formulations Against Cutaneous Herpes Simplex Virus Infections in Guinea Pigs", Antimicrob Agent Chemother 25(5): 819–823, 1984.

Stoughton, R. B., et al., "Azone ®: A New Non-Toxic Enhancer of Cutaneous Penetration", Drug. Dev. Ind. Pharm 9(4): 725–744, 1983.

Stoughton, R. B., "Azone Enhances Percutaneous Penetration", IN: Psoriasis Proceedings of the Third Int'l Sump., 397–8, 1982.

Stoughton, R. B., "Enhanced Percutaneous Penetration with 1-Dodecylazacycloheptan-2-one", Archives of Derm 118:474–477, 1982.

Sugibayashi, K., et al., "Effect of the Absorption Enhancer, Azone, on the Transport of 4-Fluorourcil Across Hairless Rat Skin", J. Pharm Pharm 37(8):578–580, 1985.

Toutitou, E., et al., "Effect of Propylene Glycol, Azone and N-Decylmethyl Suphoxide on Skin Permeation (List continued on next page.)

OTHER PUBLICATIONS

Kinetice of 5-Fluorouracil," *Int. J. Pharm* 1(27):89-98, 1985.

Wooton, P. K., et al., "Vehicle Effect on Topical Drug Delivery. III. Effect of Azone on the Cutaneous Permeation of Metronidazole and Propylene Glycol", *Int J Pharm* 1(24): 19-26, 1985.

Rajadkyaksha, V., et al., "Transdermal Delivery of ISDN from Hercon Patches Containing Azone", Proceed Intern Symp Control Rel Biact Mater, 12 (222-323), 1985.

Zoler, M. L., "Skin Penetration of Antiherpes Drugs Can Be Enhanced by Azone", Dermatology Times 5(2), 1984.

Hadgraft, J., "Percutaneous Absorption", Cos & Toiletries 100, 32-28, 1985.

Mehr, A. Z., "Evaluation of Commercial and Experimental Repellents Against Xenopsylla Cheopis (Siphonaptera: Pulicidae)", *J. Med. Entomol*, vol. 21, No. 6: 665-669.

Skinner, W. A., et al., "Tick Repellents II: N-Substituted Azacyclopentanones and Azacyclopentenones", J Pharm Sci 72(11):1354, 1983.

Vaidyanathan, R., et al., "Dodecylazacycloheptan-2-One (Azone ®) Enhanced Delivery of Drugs into the Epidermis I: Effect of Enhancer Concentration on the Permeability of Select Compounds." Abstract No. 97, *Pharm Sci* 12(2): 126, 1982.

Vaidyanathan, R., et al., "Dodecylazacycloheptan-2-One (Azone ®) Enhanced II: Permeation of Ara-A-5'-Valerate Through Hairless Mouse Skin From Prototype Formulations", Abstract No. 98, *Pharm Sci* 12(2): 126, 1982.

METHODS FOR ADMINISTRATION USING 1-SUBSTITUTED AZACYCLOALKANES

This application is a continuation of Ser. No. 824,845, filed Jan. 31, 1986 now abandoned.

BACKGROUND OF THE INVENTION

1. Field of the Invention

This invention relates to compositions comprising a physiologically-active agent and a 1-alkyl azacycloalkane, which is substituted by oxygen or sulfur atoms pendant from any of the carbon atoms alpha to the nitrogen atom, including the 1-alkyl alpha carbon atom, in an amount effective to enhance the penetration of the physiologically-active agent through the skin or other membrane of the body of an animal.

2. Background of the Art

Many physiologically active agents are best applied topically to obtain desirable results. Topical application, as contrasted to systemic application, can avoid metabolic degradation of the agents, largely avoids side effects of the agents and permits high local concentrations of the agents.

The greatest problem in applying physiologically active agents topically is that the skin is such an effective barrier to penetration. The epidermis of the skin has an exterior layer of dead cells called the stratum corneum which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use to treat such conditions as inflammation, acne, psoriasis, herpes simplex, eczema, infections due to fungus, virus, or other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to locally affected parts of the body through the vehicle system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide.

The 1-lower alkyl substituted azacyclopentan-2-ones having 1–4 carbon atoms in the alkyl group are known to moderately enhance percutaneous absorption of chemicals, e.g. drugs. It was earlier recognized that it would be desirable to obtain the same or higher level of percutaneous absorption with substantially lower concentrations of the penetration-enhancing compound. Therefore, a new class of N-substituted azacycloalkan-2-ones were invented having the desired properties. This new class of penetration-enhancing agents are described in U.S. Pat. Nos. 3,989,815; 3,989,816; 3,991,203; 4,122,170; 4,316,893; 4,405,616; 4,415,563; 4,423,040; 4,424,210; and 4,444,762, which are hereby incorporated by reference.

It is an object of this invention to provide new penetration-enhancing agents having the desirable property of enhancing the percutaneous absorption of physiologically-active agents at concentrations lower than the 1-lower alkyl substituted azacyclopentan-2-ones.

It is also an object of this invention to provide penetration-enhancing agents that are equivalent to the aforesaid new class penetration-enhancing agents described in the above U.S. patents.

Other objects and advantages of the instant invention will be apparent from a careful reading of the specification below.

In this description, the term "animal" includes human beings as well as other forms of animal life, and especially domesticated animals and pets.

SUMMARY OF THE INVENTION

This invention relates to compositions for carrying physiologically active agents through body membranes such as skin and for retaining these agents in body tissues. More specifically, the invention relates to compositions useful in topically administering a physiologically active agent to a human or animal comprising the agent and an effective, non-toxic amount of a compound having the structural formula

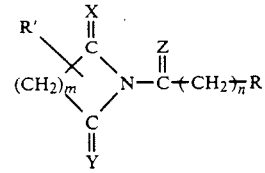

wherein each X, Y and Z may represent oxygen, sulfur or two hydrogen atoms, provided however that, when Z represents two hydrogen atoms, both X and Y represent oxygen or sulfur and when Z represents oxygen or sulfur at least one of X and Y must represent oxygen or sulfur; m is 2–6; R' is H or a lower alkyl group having 1–4 carbon atoms; n is 0–16 and R is —$CH_3$,

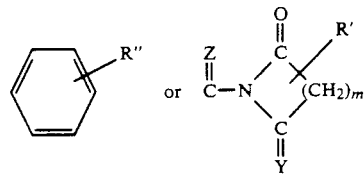

wherein R" is H or halogen.

Preferably R is —$CH_3$ and R' is H.

In a more preferred embodiment of the present invention R is —$CH_3$, R' is H and m equals 4. Even more preferably n is 4–17, e.g. 10.

It has been found that the physiologically active agents are carried through body membranes by the above penetration-enhancing agents and are retained in body tissue.

The invention further relates to the penetration-enhancing agents themselves and their method of making.

DETAILED DESCRIPTION OF THE INVENTION

The N-alkyl substituted azacycloalkanes useful as penetration-enhancing additives in the compositions of the instant invention may be made by the methods described below. Typical examples of compounds represented by the above structural formula include:

1-n-dodecylazacycloheptan-2,7-dione
1-n-dodecanoylazacycloheptan-2-one
1-n-Octadecanoylazacycloheptan-2-one
1-n-Myristoylazacycloheptan-2-one
1-n-Decanoylazacycloheptan-2-one
1-n-Undecanoylazacycloheptan-2-one
1-n-Tridecanoylazacycloheptan-2-one
1,1'-sebaccylbisazacycloheptan-2-one
1-(4-phenylbutyryl)azacyclohexan-2-one
1-n-hexanoylazacyclooctan-2-one
1,1'-adipoylbisazacycloheptan-2-one
1,1'-adipoyldiazacyclopentan-2-one
1-n-butanoylazacycloheptan-2-one
1-n-heptanoylazacycloheptan-2-one
1-n-pentanoylazacycloheptan-2-one
1-n-hexanoylazacycloheptan-2-one
1-n-octanoylazacycloheptan-2-one
1-n-nonancylazacycloheptan-2-one
1,1'-azelaoylbisazacycloheptan-2-one
1,1'-succinylbisazacycloheptan-2-one
1,1'-suberoylbisazacycloheptan-2-one
1,1'-pimeloylbisazacycloheptan-2-one
1-n-butanoylazacyclooctan-2-one
1-n-pentanoylazacyclohexan-2-one
1-n-butanoneazacyclopentan-2-one
1-n-undecanoylazacyclopentan-2-one
1-n-decanoylazacyclopentan-2-one
1-n-octanoylazacyclopentan-2-one
1-n-octanoylazacyclohexan-2-one
1-n-dodecanoylazacyclopentan-2-one
1-n-dodecylazacyclohexan-2-one
1-n-octadecanoylazacyclohexan-2-one
1-n-hexanoylazacyclohexan-2-one
1-n-butanoylazacyclohexan-2-one
1-n-pentanoylazacyclopentan-2-one
1-n-hexanoylazacyclopentan-2-one Certain of the compounds represented by the above general formula, wherein Z is oxygen, may be prepared by reacting the corresponding azacycloalkan-2-one with an alkanoyl halide in the presence of a base, e.g. sodium hydride. The reaction is carried out under anhydrous conditions in a hydrocarbon solvent, for example, dry toluene at reflux temperature for about 10 to 72 hours in an inert atmosphere, for example, nitrogen. This method is outlined below:

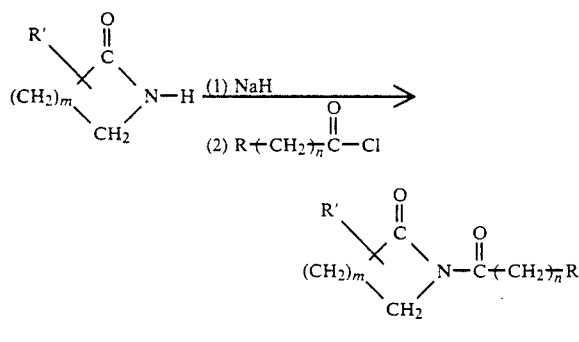

Any of the above compounds, wherein X, Y or Z is oxygen, can be converted to the corresponding sulfur analog by reacting the oxygen-containing compound with phosphorus pentasulfide.

The amount of 1-substituted azacycloalkane which may be used in the present invention is an effective, non-toxic amount for enhancing percutaneous absorption. Generally, this amount ranges between about 0.01 to about 5 and preferably about 0.1 to 2 percent by weight of the composition.

The subject compositions may find use with many physiologically active agents which are soluble in the vehicles disclosed.

Fungistatic and fungicidal agents such as, for example, thiabendazole, chloroxine, amphotericin B, candicidin, fungimycin, nystatin, chlordantoin, clotrimazole, miconazole nitrate, pyrrolnitrin, salicylic acid, fezatione, tolnaftate, triacetin and zinc and sodium pyrithione may be dissolved in the penetration-enhancing agents described herein and topically applied to affected areas of the skin. For example, fungistatic or fungicidal agents so applied are carried through the stratum corneum, and thereby successfully treat fungus-caused skin problems. These agents, thus applied, not only penetrate more quickly than when applied in the vehicles of the prior art, but additionally enter the animal tissue in high concentrations and are retained for substantially longer time periods whereby a far more successful treatment is effected.

For example, the subject compositions may also be employed in the treatment of fungus infections on the skin caused by candida and dermatophytes which cause athletes foot or ringworm, by dissolving thiabendazole or similar antifungal agents in one of the above-described penetration-enhancing agents and applying it to the affected area.

The subject compositions are also useful in treating skin problems, such as for example, herpes simplex, which may be treated by a solution of iododeoxyuridine dissolved in one of the penetration-enhancing agents or such problems as warts which may be treated with agents such as podophylline dissolved in one of the penetration-enhancing agents. Skin problems such as psoriasis may be treated by topical application of a solution of a conventional topical steroid in one of the penetration-enhancing agents or by treatment with theophylline or antagonists of β-adrenergic blockers such as isoproterenol in one of the penetration-enhancing agents.

The subject compositions are also useful for treating mild eczema, for example, by applying a solution of fluocinolone acetonide or its derivatives; hydrocortisone, triamcinolone acetonide, indomethacin, or phenylbutazone dissolved in one of the penetration-enhancing agents to the affected area.

Examples of other physiologically active steroids which may be used with the vehicles include corticosteroids such as, for example, cortisone, cortodoxone, flucetonide, fluorocortisone, difluorsone diacetate, flurandrenolone acetonide, medrysone, amcinafel, amcinafide, betamethasone and its esters, chloroprednisone, clocortelone, descinolone, desonide, dexamethasone, dichlorisone, defluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

The subject compositions are also useful in antibacterial chemotherapy, e.g. in the treatment of skin conditions involving pathogenic bacteria. Typical antibacterial agents which may be used in this invention include sulfonamides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc.

The subject compositions are also useful in protecting ultra-sensitive skin or even normally sensitive skin from damage or discomfort due to sunburn. Thus, dermatitis actinica may be avoided by application of a sunscreen, such as para-aminobenzoic acid or its well-known derivatives dissolved in one of the above-described penetration-enhancing agents, to skin surfaces that are to be exposed to the sun; and the protective paraaminobenzoic acid or its derivatives will be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultraviolet screening ingredients in the carriers of the prior art are washed off the skin when it is immersed in water.

The subject compositions may also find use in treating scar tissue by applying agents which soften collagen, such as aminopropionitrile or penicillamine dissolved in one of the penetration-enhancing agents of this invention topically to the scar tissue.

Agents normally applied as eye drops, ear drops, or nose drops are more effective when dissolved in the penetration-enhancing agents of this invention.

Agents used in diagnosis may be used more effectively when applied dissolved in one of the penetration-enhancing agents of this invention. Patch tests to diagnose allergies may be effected promptly without scratching the skin or covering the area subjected to an allergen when the allergens are applied in one of the penetration-enhancing agents of this invention.

The subject compositions are also useful for topical application of cosmetic or esthetic agents. For example, compounds such as melanin-stimulating hormone (MSH) or dihydroxyacetone and the like are more effectively applied to skin to stimulate a suntan when they are dissolved in one of the penetration-enhancing agents of this invention. The agent is carried into the skin more quickly and in greater quantity when applied in accordance with this invention. Hair dyes also penetrate more completely and effectively when dissolved in one of the penetration-enhancing agents of this invention.

The effectiveness of such topically applied materials as insect repellants or fragrances, such as perfumes and colognes, can be prolonged when such agents are applied dissolved in one of the penetration-enhancing agents of this invention.

It is to be emphasized that the foregoing are simply examples of physiologically active agent including therapeutic and cosmetic agents having known effects for known conditions, which may be used more effectively for their known properties in accordance with this invention.

In addition, the penetration-enhancing agents of the present invention may also be used to produce therapeutic effects which were not previously known That is, by use of the penetration-enhancing agents described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from exposure of the entire body to griseofulvin and the fact that only the outer layers of affected skin need to be treated Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which would cause sufficient retention of griseofulvin in the skin to be useful therapeutically.

However, it has now been discovered that griseofulvin, in a range of therapeutic concentrations between about 0.1% and about 10% may be used effectively topically if combined with one of the penetration-enhancing agents described herein.

As a further example, acne is the name commonly applied to any inflammatory disease of the sebaceous glands; also acne vulgaris. The microorganism typically responsible for the acne infection is Corynebacterium acnes. Various therapeutic methods for treating acne have been attempted including topical antibacterials, e.g. hexachlorophene, and systemic antibiotics such as tetracycline. While the systemic antibiotic treatments are known to be partially effective, the topical treatments are generally not effective.

It has long been known that systemic treatment of acne is not preferred because of side effects resulting from exposure of the entire body to antibiotics and the fact that only the affected skin need be treated. However, despite a long-felt need for a topical treatment for acne, antibiotics generally have been used only systemically to treat acne because there was not heretofore known an antibacterial formulation which could be used topically which would be effective therapeutically in the treatment of acne. However, it has now been discovered that antibiotics, especially those of the lincomycin and erythromycin families of antibiotics, may be used in the treatment of acne topically if combined with one of the penetration-enhancing agents described herein.

The antibiotics composition so applied is carried into and through the epidermis and deeper layers of the skin as well as into follicles and comedones (sebum-plugged follicles which contain C. acnes) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, antifungal agents, antibacterial agents, antineoplastic agents, allergens, antihistaminic agents, anti-inflammatory agents, ultraviolet screening agents, diagnostic agents, perfumes, insect repellants, hair dyes, etc.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freons, ethyl alcohol, polyvinylpyrrolidone, propylene glycol, fragrances, gel-producing materials, mineral oil, stearyl alcohol, stearic acid, spermaceti, sorbitan monooleate, "Polysorbates", "Tweens", sorbital, methyl cellulose, etc.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of physiologically active agent may often be decreased from that generally applicable. In accordance with the usual prudent formulating practices, a dosage near the lower end of the useful range of the particular physiologically active agent may be employed initially and the dosage increased as indicated from the observed response, as in the routine procedure of the physician.

The invention is further illustrated by the following examples which are illustrative of various aspects of the invention, and are not intended as limiting the scope of the invention as defined by the appended claims.

EXAMPLE 1

Sodium hydride [5.14 g (50% oil dispersion); 0.107 mol] in 100ml of dry toluene was added to a 500 ml, 3-necked flask fitted with a mechanical stirrer. Azacycloheptan-2-one (10.07 g; 0.089 mol) was dissolved in 50ml of dry toluene with slight warming and added to the sodium hydride suspension dropwise at room temperature. The suspension was stirred at room temperature for 1 hour. n-Dodecanoyl chloride (19.39 g; 0.089 mol) in 10ml of dry toluene was added dropwise to the mixture and after the addition was complete, the mixture was stirred overnight at room temperature. The mixture was then washed with water, and the organic layer separated, dried with MgSO$_4$, and concentrated. The resulting yellow oil was distilled 160° C./0.35mm to yield 1-n-dodecanoylazacycloheptan-2-one as clear oil.

EXAMPLE 2

The compound of Example 1 was tested as a penetration enhancing agent according to the below procedure:

Skin from female hairless mice, 4–6 weeks old, was removed from the animal and placed over penetration wells with normal saline bathing the corium. A plastic cylinder 1.4 cm in diameter was glued onto each piece on the epidermal side. 0.1% triamcinolone acetonide $^3$H was applied (0.01 cc) to the epidermal surface within the 1.4 cm diameter cylinder. The skin was incubated at room temperature and ambient humidity.

At 6 hours and 24 hours, 2 cc were removed from the 10 cc reservoir of normal saline bathing the corium. The 2 cc of normal saline removed were replaced after the 6 hour sample with 2 cc of normal saline.

The 2 cc aliquots were put into scintillation fluid and the radioactivity determined in a scintillation counter. The amount penetrating was calculated as per cent of dose applied.

In every experiment the $^3$H triamcinolone acetonide was dissolved in ethanol and the penetration-enhancing agent to be tested was added to the desired concentration.

The controls were ethanol, alone, and 1-n-dodecylazacycloheptan-2-one, a compound described in the U.S. patents, noted above, as having superior penetration-enhancing properties. Five separate tests for the compound of Example 1 and the controls were made and the results averaged.

The results, as reported in the Table below, show that the compound of Example 1 has superior penetration-enhancing properties.

TABLE

| Penetration-Enhancing | Percent Penetration | |
|---|---|---|
| Agent | 6 hr. | 24 hr. |
| Example 1 | 18.96 | 74.34 |
| 1-n-Dodecylcycloheptan-2-one | 16.64 | 60.94 |
| Ethanol (only) | 0.56 | 6.78 |
| Ethanol (only, repeat) | 0.5 | 5.64 |

As can be shown from the above results the compound of Example 1 shows surprisingly better penetration-enhancing properties than 1-n-dodecylcycyloheptan-2-one.

EXAMPLE 3

The following formulation is prepared:

|  | Solution (%) |
|---|---|
| Griseofulvin | 1 |
| 1-n-Dodecanoylazacycloheptan-2-one | 1 |
| Isopropyl myristate | 5 |
| Fragrance | 0.1 |
| Ethanol | 92.9 |

This formulation is effective in the treatment of fungus infections.

EXAMPLE 4

An aerosol form of the formulation of Example 3 is prepared by preparing the following mixture:

| Formulation | 25% |
|---|---|
| Freon[1] | 75% |

[1]Freon is 75/25 Freon 114/12.

EXAMPLE 5

The following cream formulation is prepared:

|  | % |
|---|---|
| Clindamycin base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-n-Dodecanoylazacycloheptan-2-one | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 6

The following solution formulations are prepared:

|  | A (%) | B (%) |
|---|---|---|
| Clindamycin base | — | 1.0 |
| Clindamycin phosphate acid | 1.3 | — |
| Sodium hydroxide | 0.077 | — |
| 1.0M Hydrochloric acid | — | 2.27 |
| Disodium edetate:2H$_2$O | 0.003 | 0.003 |
| Fragrances | 0.5 | 0.5 |
| 1-n-Dodecanoylazacycloheptan-2-one | 1.0 | 1.0 |
| Purified water | 20.0 | 17.73 |
| Isopropanol | 77.12 | 77.497 |

These solutions are effective for the treatment of acne in humans.

EXAMPLE 7

The following solution formulation is prepared:

|  | % |
|---|---|
| Neomycin sulfate | 0.5 |
| Lidocaine | 0.5 |
| Hydrocortisone | 0.25 |
| 1-n-Dodecanoylazacycloheptan-2-one | 0.5 |
| Propylene glycol | 98.25 |

This solution is effective for the treatment of otitis in domestic animals.

EXAMPLE 8

The following sunscreen emulsion is prepared:

|  | % |
|---|---|
| p-aminobenzoic acid | 2.0 |
| Benzyl alcohol | 0.5 |
| 1-n-Dodecanoylazacycloheptan-2-one | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water | 64.0 |

EXAMPLE 9

The following antineoplastic solution is prepared:

|  | % |
|---|---|
| 5-Fluorouracil | 5.0 |
| 1-n-Dodecanoylazacycloheptan-2-one | 0.1 |
| Polyethylene glycol | 5.0 |
| Purified water | 89.9 |

EXAMPLE 10

The following insect repellant atomizing spray is prepared:

|  | % |
|---|---|
| Diethyltoluamide | 0.1 |
| 1-n-Dodecanoylazacycloheptan-2-one | 0.1 |
| Ethanol | 99.8 |

EXAMPLE 11

The following lotion formulation may be prepared containing about 0.001 to 1 percent, with preferably 0.1 percent fluocinolone acetonide:

|  | % |
|---|---|
| Fluocinolone acetonide | 0.001-1 |
| Cetyl alcohol | 15.0 |
| Propylene glycol | 10.0 |
| Sodium lauryl sulfate | 15.0 |
| 1-n-Dodecanoylazacycloheptan-2-one | 1.0 |
| Water (to make 100%) |  |

The steroid is dissolved in the vehicle and added to a stirred, cooling melt of the other ingredients. The preparation is particularly useful for the treatment of inflamed dermatoses by topical application to the affected skin area. The amount of frequency of application is in accordance with standard practice for topical application of this steroid. Penetration of the steroid into the inflamed tissue is enhanced and a therapeutic level is achieved more rapidly and sustained for longer duration than when the steroid is applied in conventional formulations.

EXAMPLE 12

Examples 3-11 are repeated except that 1-n-dodecanoylazacycloheptan-2-one is replaced with the following penetration-enhancing agents:
1-n-dodecylazacycloheptan-2,7-dione
Comparable results are obtained.

While particular embodiments of the invention have been described it will be understood of course that the invention is not limited thereto since many obvious modifications can be made and it is intended to include within this invention any such modifications as will fall within the scope of the appended claims.

Having now described the invention, we claim.

1. A method for administering an effective amount of a therapeutically active agent through the skin or other membrane of a human or animal and for retaining said agent in the body tissues which comprises contacting said therapeutically active agent with said skin or other membrane in the presence of an amount for enhancing percutaneous absorption thereof, of a nontoxic compound having the structural formula

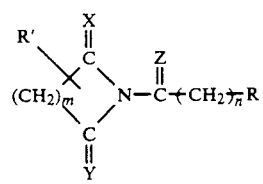

wherein each X, Y and Z may represent oxygen, sulfur or two hydrogen atoms, provided, however that, when Z represents two hydrogen atoms, both X and Y represent oxygen or sulfur and when Z represents oxygen or sulfur at least one of X and Y must represent oxygen or sulfur; m is 2-6; R' is H or a lower alkyl group having 1-4 carbon atoms; n is 0-16 and R is —CH$_3$,

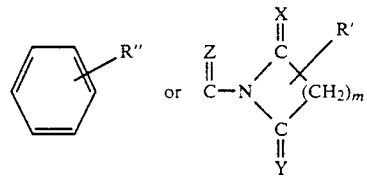

wherein R" is H or halogen, and retaining said compound in the body tissues.

2. The method of claim 1 wherein the therapeutically active agent is an antifungal agent.

3. A method for enhancing penetration of a pharmaceutically active agent into a human or animal which comprises contacting said pharmaceutically active agent with the skin or other membrane of said human or animal in the presence of a non-toxic, effective penetrating amount of a compound having the structural formula

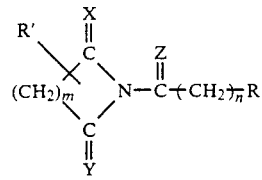

wherein each X, Y and Z may represent oxygen, sulfur or two hydrogen atoms, provided, however that, when Z represents two hydrogen atoms, both X and Y represent oxygen or sulfur and when Z represents oxygen or sulfur at least one of X and Y must represent oxygen or sulfur; m is 4; n is 4–17; r is —$CH_3$, and R' is H, and retaining the penetration enhancer in the body tissues.

4. The method of claim 3 wherein the therapeutically active agent is an antifungal agent.

* * * * *